(12) United States Patent
Melsheimer (10) Patent No.: US 7,963,948 B2
(45) Date of Patent: Jun. 21, 2011

(54) HEMOSTASIS VALVE SYSTEM

(75) Inventor: Jeffry S. Melsheimer, Springville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 143 days.

(21) Appl. No.: 12/366,935

(22) Filed: Feb. 6, 2009

(65) Prior Publication Data

US 2010/0204655 A1   Aug. 12, 2010

(51) Int. Cl.
*A61M 5/178* (2006.01)
(52) U.S. Cl. .............................. 604/167.03; 604/167.06
(58) Field of Classification Search ............. 604/167.01, 604/167.03, 167.06, 164.01, 164.12, 256, 604/264; 251/149.1, 149.2
See application file for complete search history.

(56) References Cited

U.S. PATENT DOCUMENTS

| | | | |
|---|---|---|---|
| 4,430,081 A | 2/1984 | Timmermans | 604/256 |
| 5,006,113 A | 4/1991 | Fischer | 604/167 |
| 5,158,553 A | 10/1992 | Berry et al. | 604/248 |
| 5,267,966 A | 12/1993 | Paul | 604/167 |
| 5,334,164 A | 8/1994 | Guy et al. | 604/248 |
| 5,350,363 A | 9/1994 | Goode et al. | 604/167 |
| 5,484,418 A | 1/1996 | Quiachon et al. | 604/167 |
| 6,416,499 B2 | 7/2002 | Paul, Jr. | 604/256 |
| 7,172,580 B2 | 2/2007 | Hruska et al. | 604/248 |
| 2006/0135972 A1* | 6/2006 | Zeiner | 606/167 |
| 2006/0135977 A1* | 6/2006 | Thompson et al. | 606/185 |
| 2007/0078395 A1 | 4/2007 | Valaie | 604/164.01 |
| 2008/0157017 A1 | 7/2008 | Macatangay et al. | 251/314 |

* cited by examiner

*Primary Examiner* — Nicholas D Lucchesi
*Assistant Examiner* — Laura A Bouchelle
(74) *Attorney, Agent, or Firm* — Brinks Hofer Gilson & Lione (57) ABSTRACT

A hemostasis valve system for controlling a flow of fluid includes a housing having a chamber therein, and a valve disposed in the chamber. The valve comprises a plurality of elastomeric valve members, each having opposing shaped first and second faces, a shaped inner edge portion, and a shaped outer edge portion. The valve members are collectively structured and arranged in the valve such that the shaped faces and the shaped inner edges are engaged in interlocking relationship. The valve members have sufficient elasticity to define a yieldable opening along the engaged inner edge portions upon passage therethrough of a medical interventional device.

15 Claims, 7 Drawing Sheets

HEMOSTASIS VALVE SYSTEM

BACKGROUND

1. Technical Field

The present invention relates to a valve system. More particularly, the invention relates to a hemostasis valve system for use with a medical device, such as an introducer, to permit substantially leak-free passage therethrough of an interventional device for insertion into a body vessel.

2. Background Information

A variety of well-known medical procedures are performed by introducing an interventional device, such as a catheter, trocar, sheath, stent and the like, into a vessel in a patient's body. Typical procedures for introducing an interventional device into a blood vessel include the well-known Seldinger technique. The Seldinger technique involves opening a blood vessel with a needle, inserting a wire guide into the vessel through the lumen of the needle, withdrawing the needle and inserting a dilator over the wire guide. The dilator is located inside an introducer sheath which is also inserted into the vessel, and the dilator is sealed to the sheath by a hemostasis valve through which the dilator passes. The dilator is thereafter removed, and an interventional device is inserted through the sheath and hemostasis valve into the vessel.

During performance of the Seldinger technique and other interventional procedures, care must be taken to avoid the undesirable introduction or leakage of air into the vessel (air embolism), as well as the undesirable leakage of blood, other bodily fluids or cavity-pressurizing gas from the patient. As procedures for introducing catheters and other interventional devices have become more widely accepted, the procedures have become more diverse, and the variety of sizes and types of such devices employed has grown dramatically. As a result, the risk of inward or outward leakage of fluids has increased.

One known way to minimize such leakage is to provide one or more disk-like gaskets (often referred to as check valves) in an elongated passageway of a device through which fluids may pass into or out of the body. Such devices are generally positioned in a housing at a proximal end portion of the introducer, between a main body portion and an end cap. The disks typically include one or more slits, apertures, or other configurations extending at least partially through the disk to provide a sealable path to permit insertion of the medical interventional device through the disk, and to substantially prevent the backflow of fluids. Examples of such disks are provided in, among others, U.S. Pat. Nos. 4,430,081, 5,006,113 and 6,416,499, incorporated by reference herein. Such valves are now well known in the medical arts, and additional discussion of their use and function is not necessary for an understanding of the present invention.

Frequently, it is necessary to replace a previously-inserted medical interventional device with another interventional device of a different diameter, or with a different type of device. Such exchanges are normally made over a wire guide, wherein the old device is withdrawn over the wire guide, and the new device is thereafter inserted into the body vessel over the existing wire guide or a newly-inserted wire guide. In many such cases, elastomeric hemostasis valves are provided in an attempt to minimize leakage of blood back through the introducer. Such valves are dependent upon the elasticity of the valve body, such as valve disks, and its ability to draw back upon itself to seal any gap created upon insertion or withdrawal of a device through the valve.

Known slitted hemostasis valves generally include one or more disks having slits that criss-cross and span a center portion of the valve disk, or a hole disposed through the center of the disk. As the interventional device is passed through the center of a slit valve disk, the slits open outwardly and form one or more generally "V"-shaped openings that are disposed along the outer surface of the interventional device. Such linear-type openings often do not form tight seals, and inherently create gaps that permit the leakage of at least some fluid. As a result, hemostasis valve systems may comprise two or three such valve members that are aligned in the valve housing in a manner such that the slit portions are not in axial alignment. Although this arrangement may reduce the amount of leakage compared to the use of a single valve member, the presence of the gaps continues to provide a conduit from which some leakage may occur. Similarly, the various flaps resulting from the slits do not always re-set in the proper manner following passage of the interventional device, thereby creating additional gaps through which fluid may leak.

In addition to the foregoing, when larger slitted valve disks are utilized, the interventional devices may tear the portion of the valve disk upon insertion that extends radially beyond the slits. This is particularly true when larger size interventional devices are inserted. In such cases, multiple valve disks must generally be incorporated in order to provide a reasonable degree of confidence that the valve system will continue to provide at least some leakage control. In some cases, the damage to the valve may be so severe, that it may be necessary to incorporate another type of valve, such as a Tuohy-Borst type valve, to the introducer.

Similarly, when smaller slitted valve disks are utilized, the valves are also subject to tearing when smaller size interventional devices are passed therethrough. Small size interventional devices are often delicate, and possess little hoop strength. When such devices pass through a small valve member, the thickness and strength of the valve member may cause damage to the delicate structure upon passage therethrough of the interventional device. When small disks are used, the clearance between the opening in the disk and the interventional device can be so slight that it may be difficult to insert and/or withdraw the interventional device. In addition, on some occasions, additional small diameter tubing must be used to keep the valve open so that a catheter may be passed therethrough. When additional equipment is required, such as a small diameter tube or a Tuohy-Borst valve as described, the surgeon's hands, and attention, may be unduly distracted at the very time when all possible focus should be on the primary task at hand.

When one or more valve disks having a hole through the center of the disk are used, the disks will only recover back to the size of the center hole following removal of the catheter. As a result, the respective center holes allow leakage once the catheter is removed. Such valves may be satisfactory when there is no need to remove the catheter that seals the opening; however, they can be problematic when the catheter is removed and the center opening is left unoccluded.

It is desired to provide a hemostasis valve system for a medical device that provides an effective seal for controlling a flow of fluid, and that avoids the problems encountered with prior art seals.

BRIEF SUMMARY

The present invention addresses the problems of the prior art. In one form thereof, the present invention relates to a hemostasis valve system for controlling a flow of fluid. The valve system comprises a housing having a proximal end, a distal end, and a chamber disposed therebetween; and a valve disposed in the chamber. The valve comprises a plurality of interlocked elastomeric valve members. Each of the valve members has opposing shaped first and second faces, a shaped inner edge portion, and a shaped outer edge portion. The valve members are collectively structured and arranged in the valve such that the shaped faces and the shaped inner edges are engaged in the interlocking relationship. The valve members have sufficient elasticity to define a yieldable opening along the engaged inner edge portions upon passage therethrough of a medical interventional device.

In another form thereof, the invention comprises an apparatus for use in controlling a flow of fluid while introducing a medical interventional device into a body vessel of a patient. The apparatus comprises a housing having a chamber, a valve disposed in the chamber, and a sheath. The valve comprises a plurality of elastomeric valve members. Each of the valve members has opposing shaped first and second faces, a shaped inner edge portion, and a rounded outer edge portion. The valve members are collectively structured and arranged such that the shaped faces and the shaped inner edges are engaged in interlocking relationship to define a generally annular structure. The shaped inner edge portions of the elastomeric members are arranged to define a sealable passageway. The sheath is sized for passage through the sealable passageway, and is extendable distally therefrom into the body vessel.

In yet another form thereof, the invention comprises a valve for a fluid flow path. The valve comprises a plurality of elastomeric valve members. Each of the valve members has opposing shaped first and second faces, a shaped inner edge portion, and a rounded outer edge portion. Each of the shaped first and second faces comprises respective first and second elevations, and each of the shaped inner edge portions includes a concave portion and a convex portion. The valve members are collectively structured and arranged such that the shaped faces and shaped inner edges are engaged in interlocking relationship, whereby a generally disk-shaped structure is defined thereby. The valve members have sufficient elasticity to define a yieldable opening along the engaged inner edge portions for passage therethrough of a medical interventional device. In one preferred form, each of the shaped inner edge portions includes a feather extension.

DETAILED DESCRIPTION OF THE DRAWINGS AND THE PRESENTLY PREFERRED EMBODIMENTS

For purposes of promoting an understanding of the present invention, reference will now be made to the embodiments illustrated in the drawings, and specific language will be used to describe the same. It should nevertheless be understood that no limitation of the scope of the invention is thereby intended, such alterations and further modifications in the illustrated apparatus, and such further applications of the principles of the invention as illustrated therein being contemplated as would normally occur to one skilled in the art to which the invention relates.

The present invention relates to a hemostasis valve system for use in combination with a medical device, such as an introducer. In the following discussion, the terms "proximal" and "distal" will be used to describe the opposing axial ends of the hemostasis valve system, as well as the axial ends of other components of the system. The term "proximal" is used in its conventional sense to refer to the end of the hemostasis valve system (or component thereof) that is closer to the operator during use of the device. The term "distal" is used in its conventional sense to refer to the end of the hemostasis valve system (or component thereof) that is initially inserted into the patient, or that is closer to the patient during use.

Figure 1:
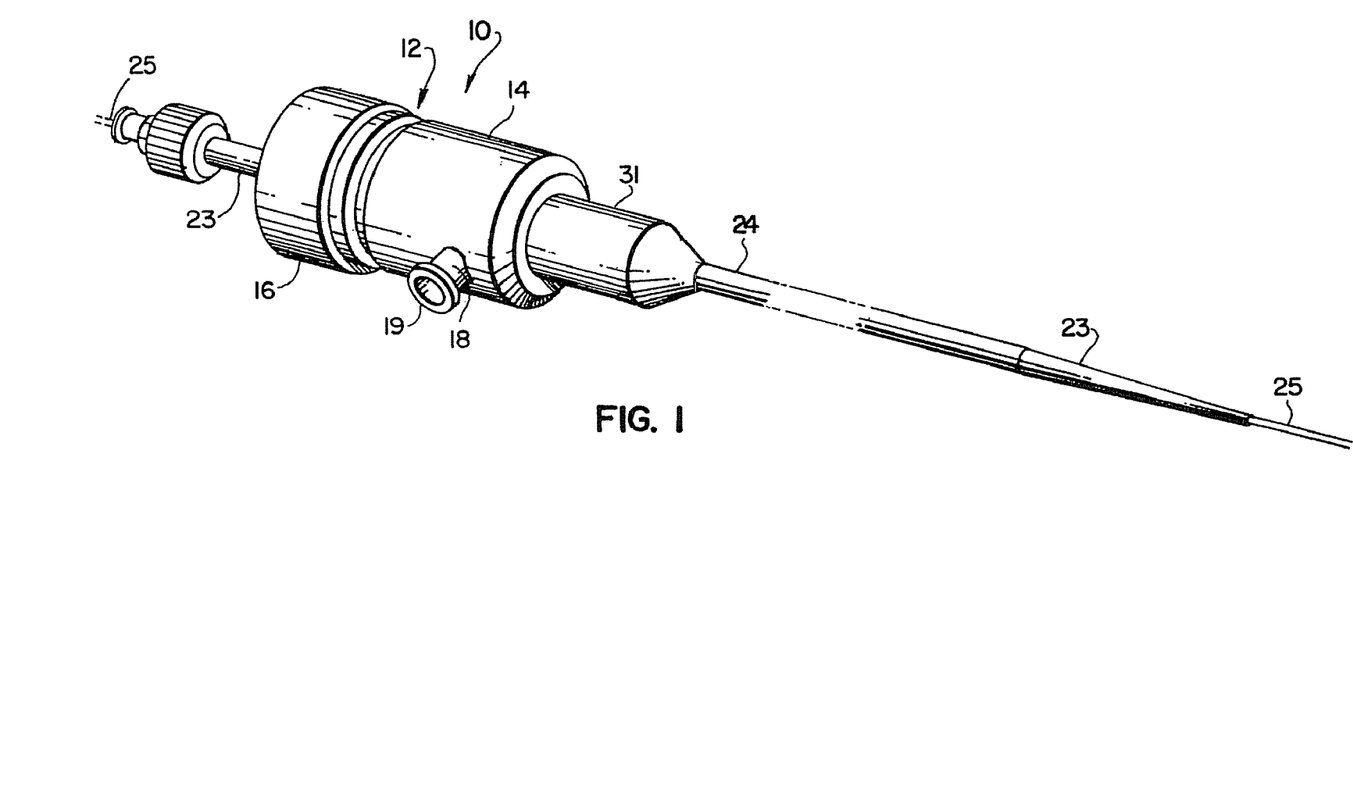
FIG. 1 is a perspective view of a hemostasis valve system according to an embodiment of the present invention, shown in combination with an introducer sheath and a dilator, and positioned over a wire guide.
Figures 2, 3:
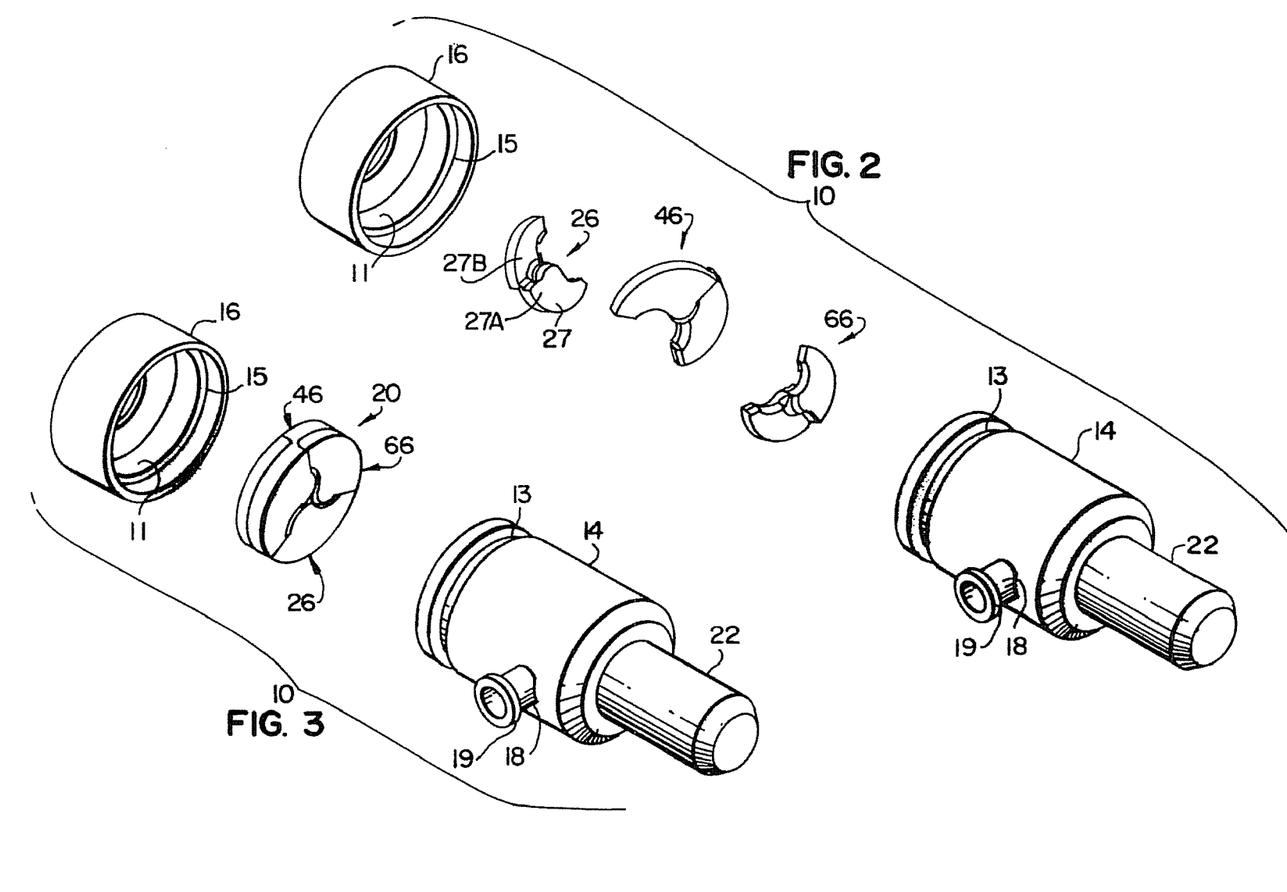
FIG. 2 is an exploded view of the hemostasis valve system of FIG. 1.
FIG. 3 is an exploded view similar to that of FIG. 2, but illustrating the interlocking arrangement of the valve members.

FIG. 1 illustrates a perspective view of a hemostasis valve system 10, according to an embodiment of the present invention. In this figure, hemostasis valve system 10 is shown in combination with an introducer sheath 24, a dilator 23, and a wire guide 25. An optional strain relief 31 is also shown at the distal end of the valve system. Hemostasis valves are commonly used in combination with introducer sheaths, dilators and wire guides, and the particular configurations of these elements shown herein for use with the hemostasis valve system 10 are only intended to represent examples of such elements that would be known to those skilled in the art. The features of hemostasis valve system 10 visible in FIG. 1 are conventional, and are common in many commercially available introducers. FIGS. 2 and 3 illustrate exploded views of one embodiment of the hemostasis valve system 10 illustrated in FIG. 1.

The embodiment of hemostasis valve system 10 illustrated herein includes a housing 12. In the embodiment shown, housing 12 comprises a main body 14 and an end cap 16. The main body may be formed of a rigid polymer, such as polycarbonate. The end cap may be formed of a lightweight, wear-resistant plastic, such as acetal resin (e.g., DELRIN®). Main body 14 and end cap 16 may be joined in any conventional fashion, such as by a screw fit, a snap fit, a friction fit, and the like. In the embodiment shown (FIGS. 2 and 3), housing 14 is provided with an external groove 13, and end cap 16 is provided with an internal rim 15. When main body 14 and end cap 16 are joined as shown in FIG. 1, rim 15 is received in groove 13 to form a locking arrangement between main body 14 and end cap 16. Those skilled in the art will appreciate that numerous alternative engagement mechanisms may be substituted, with the illustrated arrangement utilizing the groove and the rim merely representing one example.

Housing 12 may also include a side-arm spout 18 extending in a generally transverse direction from main housing body 14. Preferably, spout 18 includes a lip 19 sized and shaped, e.g., via a Luer-type connection, for threaded or like engagement with a tube or other device (not shown). A fluid or a drug may be transmitted or aspirated to or from the hemostasis valve system 10 through spout 18 in conventional fashion. The distal end of main housing body 14 includes a smaller diameter portion 22. The proximal end of introducer sheath 24, which may be provided with a slight taper if desired, extends into the interior of hemostasis valve system 10 in conventional fashion.

The exploded views of FIGS. 2 and 3 best illustrate the arrangement of housing main body 14, end cap 16, and elastomeric valve members 26, 46, 66. Valve members 26, 46, and 66 are arranged in a chamber 11 defined by an interior space of the main body 14 and end cap 16, respectively, when the main body and end cap are engaged as shown in FIG. 1. Typically, the chamber 11 will be in the interior space of the end cap 16, and the valve members will be nested therein in a manner to be described. FIG. 2 illustrates the valve members prior to their alignment in the hemostasis valve system. FIG. 3 illustrates the valve members aligned in the interlocking arrangement to form hemostasis valve 20, as further described herein.

Figure 4:
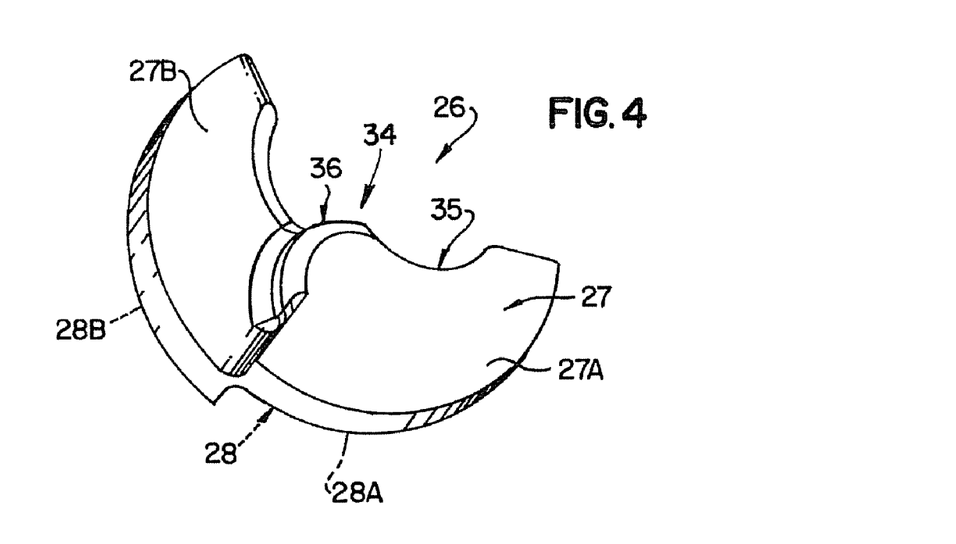
FIG. 4 is an enlarged perspective view of one embodiment of a valve member for use in the hemostasis valve system of FIG. 1.
Figure 5:
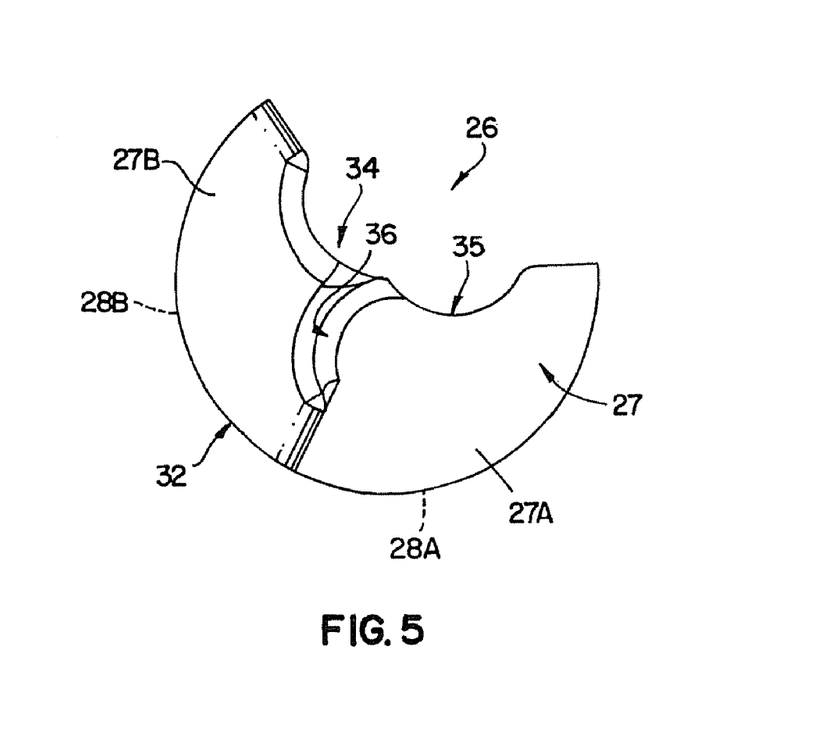
FIG. 5 is a top view of the valve member of FIG. 4.
Figure 6:
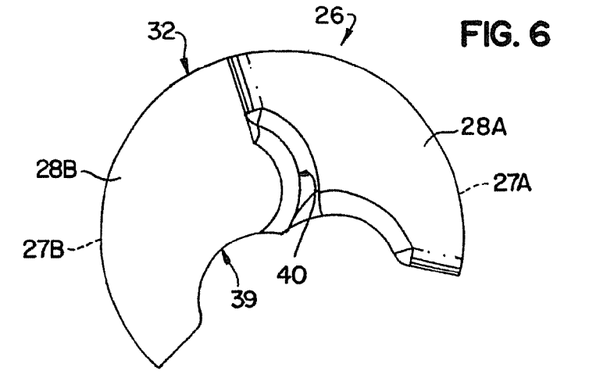
FIG. 6 is a bottom view of the valve member of FIG. 4.
Figure 7:
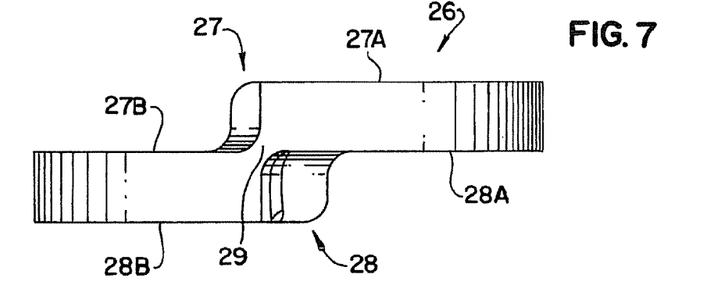
FIG. 7 is a side view of the valve member of FIG. 4.

The use of elastomeric members as hemostasis valve disks is known in the medical industry. However, the configuration and alignment of the elastomeric members in the present invention differs from that of conventional valve disks. FIG. 4 illustrates a perspective view of an embodiment of a valve member 26 suitable for use in the present invention. FIG. 5 illustrates a top view of valve member 26, FIG. 6 illustrates a bottom view of valve member 26, and FIG. 7 illustrates a side view of valve member 26. Preferably, valve members 46 and 66 are structurally identical to valve member 26, and differ only in their particular orientation in valve system 10.

Valve member 26 includes respective faces 27, 28. Each of faces 27, 28 includes at least two elevations. These elevations are best shown in FIG. 7. In the embodiment shown, face 27 includes a first elevation 27A and a second elevation 27B, respectively. Correspondingly, face 28 includes a first elevation 28A and a second elevation 28B, respectively. The respective elevations are interconnected at transition 29.

In the embodiment shown, valve member 26 also includes a rounded outer edge portion 32. This is best shown in FIGS. 5 and 6. Rounded outer edge portion 32 is complementary with rounded outer edge portions 52, 72, of valve members 46, 66, respectively, to form the generally annular outer surface of valve 20 best shown in FIGS. 3 and 9 when the valve members are arranged in an interlocking relationship.

Valve member 26 comprises a shaped inner edge portion 34. Inner edge portion 34 is shaped to be complementary with corresponding shaped inner edge portions of valve members 46, 66, respectively, such that said valve members interlockingly engage as shown and described. Preferably, the shaped structure of the inner edge includes one or more curved portions sized and shaped for engagement with complementary curved portions of another valve member as described.

In the embodiment shown, elevation 27A of face 27 includes a concave portion 35 and a convex portion 36 (FIG. 5). Similarly, elevation 27B of face 27 includes a concave portion 39 and a convex portion 40 (FIG. 6). The respective concave and convex portions of each face of valve member 26 are sized and shaped for engagement with complementary concave and convex portions in another valve member.

Figure 8:
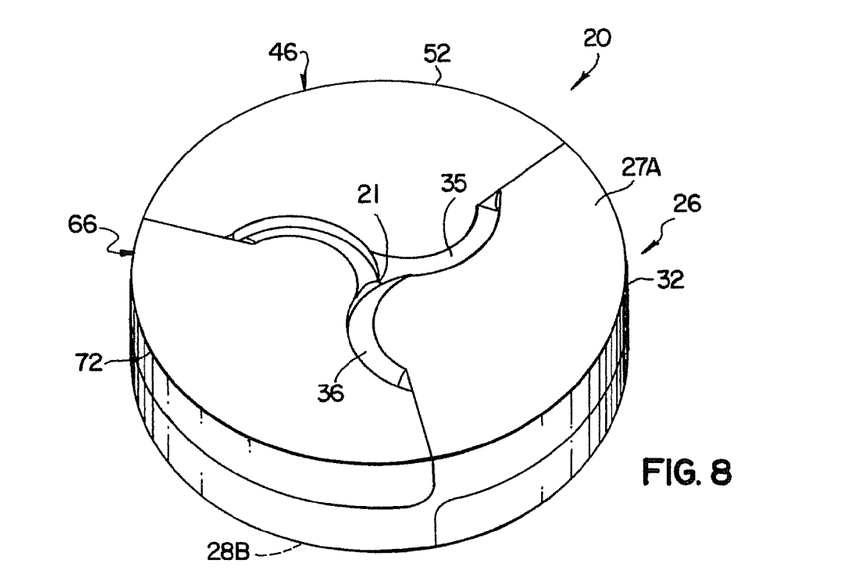
FIG. 8 is a perspective view of the valve members in an interlocking relationship.
Figure 9:
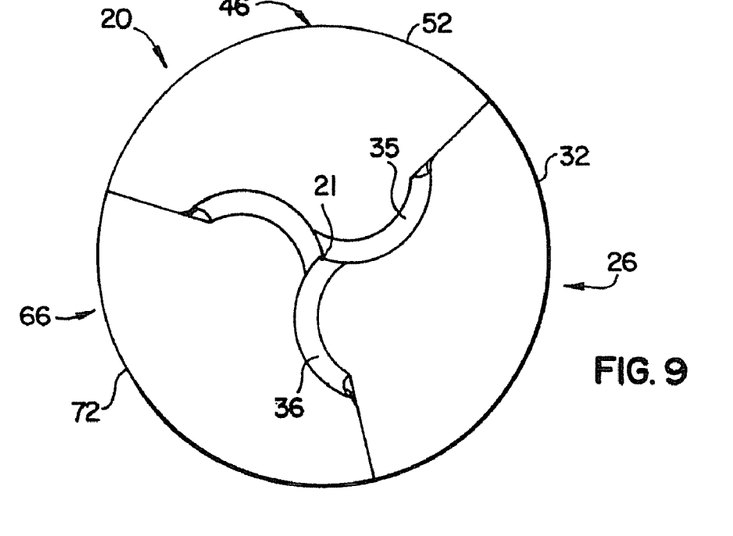
FIG. 9 is a top view of the interlocked valve members of FIG. 8.

The interlocking engagement of the respective valve members is best shown in FIGS. 8 and 9. Valve members 26, 46, 66 are oriented rotationally 120 degrees from one another. In this manner, the respective concave and convex portions of the various valve members are interlocked, and the respective elevations merge to define the annular valve 20.

When the valve members are aligned as described and shown herein, a medical interventional device, such as a catheter, may pass through an opening formed at the radial center 21 of the valve 20 (FIG. 9). Since valve members 26, 46, 66 are elastomeric, the adjoining portions of the elastomeric valve members at radial center 21 have sufficient elasticity to yield to the interventional device, and thereby define the opening to allow the interventional device to pass therethrough. Following removal of the interventional device, the valve members substantially return to a pre-stretched condition at the radial center 21.

Figure 10:
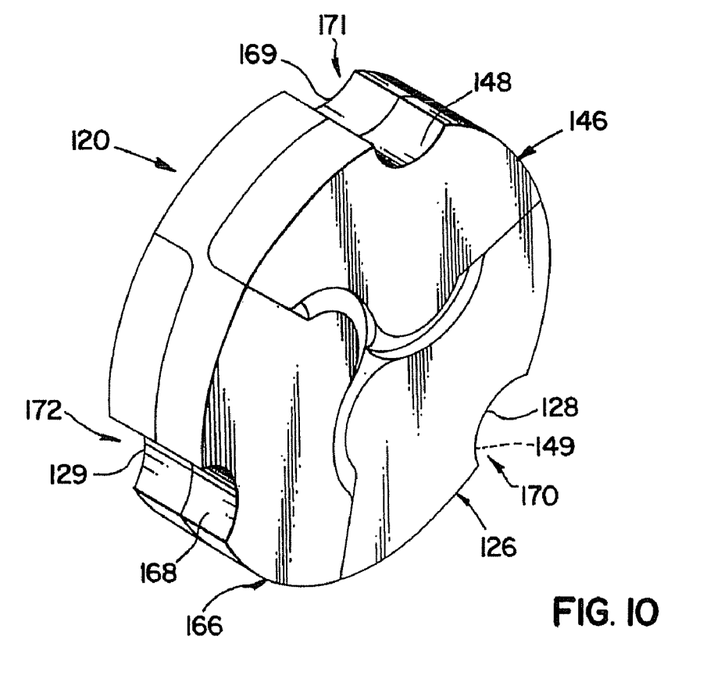
FIG. 10 is a perspective view of another embodiment of a valve, showing the valve members in interlocking relationship.

FIG. 10 illustrates another embodiment of a valve 120 that may be utilized in the inventive hemostasis valve system. FIG. 10 illustrates three valve members 126, 146, 166, shown in interlocking relationship in the same manner as valve members 26, 46, 66 shown in FIG. 8. Valve members 126, 146, 166 of FIG. 10 are structurally similar to valve members 26, 46, 66 of the preceding embodiment, with the exception that valve members 126, 146, 166 include respective notches disposed along the circumferential outer edge of each valve member. Thus, as shown, valve member 126 includes notches 128, 129. Valve member 146 includes notches 148, 149, and valve member 166 includes notches 168, 169. The respective notches are aligned in a manner such that respective grooves 170, 171, 172 are defined along the outer circumference of valve 120.

Figure 11:
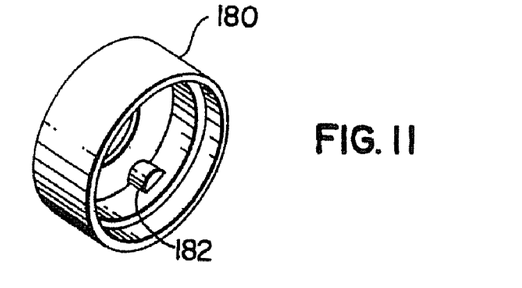
FIG. 11 is an end cap for the valve housing that has been modified to receive valve members of the type shown in FIG. 10.

In this embodiment, housing end cap 180 (FIG. 11) is provided with three ribs (only one rib 182 is visible in FIG. 11) spaced 120 degrees along its interior surface that correspond to, and receive, the three grooves 170, 171, 172 as shown in FIG. 10. This cooperating structure prevents rotation or other movement of the valve members in the housing, thereby maintaining the desired orientation of the valve members in the housing.

Although the valve members described above include notched portions that provide easy alignment of the valve members in the housing, any other configuration that is capable of accomplishing the same purpose may be substituted. For example, one or more flattened portions ("flats") can be provided along the circumference of the valve members, and complementary flattened portions can be provided on the interior surface of the end cap to receive the flats on the circumference of the valve members. Similarly, the arrangement of notches and ribs may be reversed from that described and shown herein. In other words, the valve members may include a rib-like projection from the circumferential edge, and the interior surface of the end cap may be provided with a notch or groove to receive the rib-like projections. The list of alternative cooperating structures provided herein is not intended to be exclusive, and those skilled in the art will appreciate that other complementary guide, tab, etc., structures suitable for maintaining an orientation of the valve members in the housing may be substituted for those described and shown.

Figure 12:
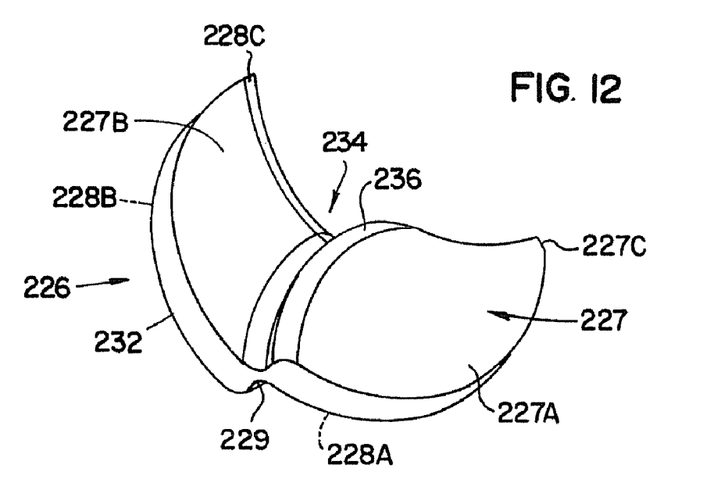
FIG. 12 is a top view of an alternative embodiment of a valve member.
Figure 13:
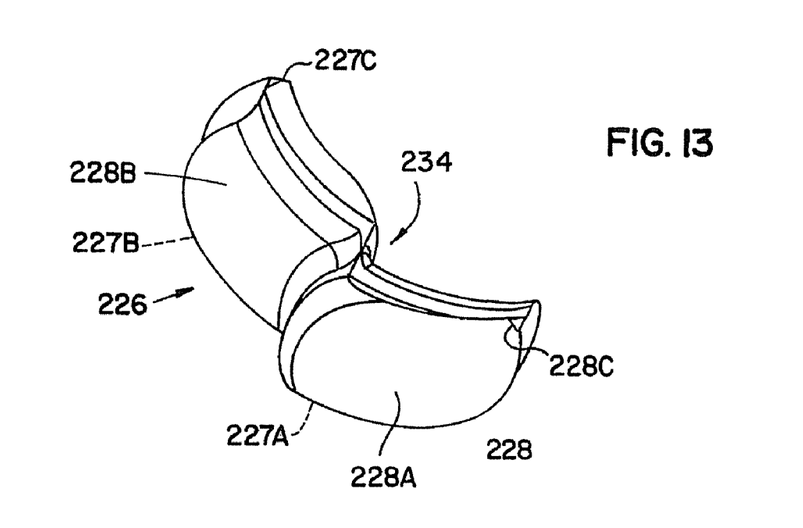
FIG. 13 is a view taken from the underside of the valve member of FIG. 12.
Figure 14:
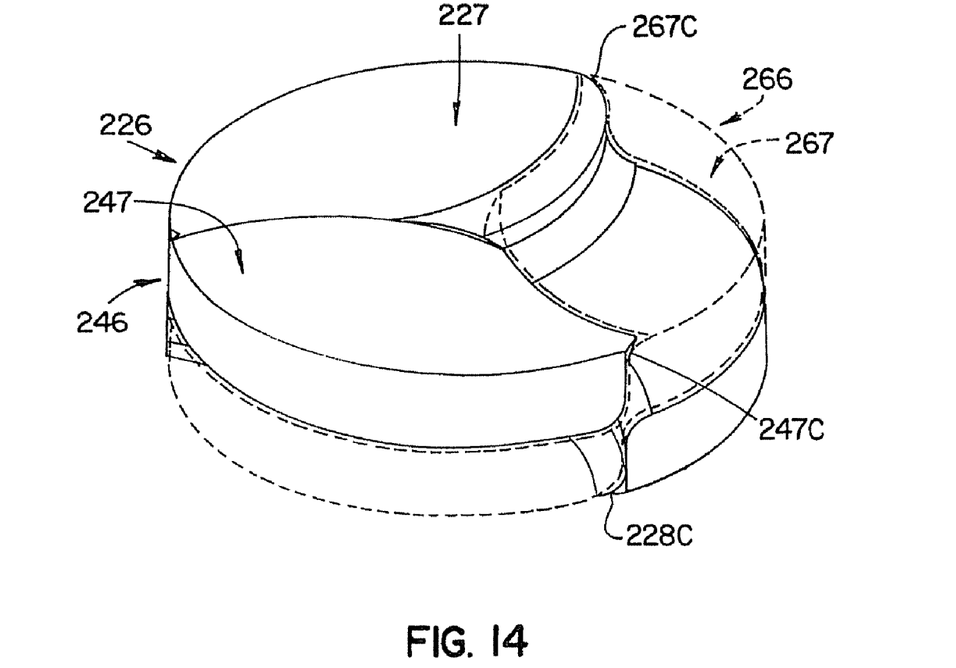
FIG. 14 is a perspective view of a valve system made up of valve members as shown in FIG. 12 in interlocking relationship, with one of the three valve members shown in phantom.
Figure 15:
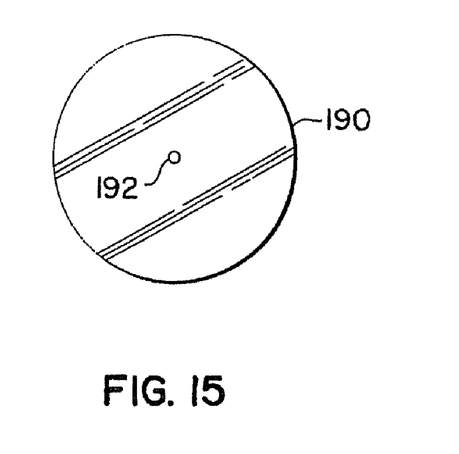
FIG. 15 is an example of an optional guide disk that may be utilized in combination with the inventive valve system.

FIGS. 12-14 illustrate another embodiment of a valve system formed from identical valve members 226, 246, 266.

FIG. 12 illustrates a view of the top of valve member 226, and FIG. 13 illustrates a view of the underside of valve member 226. FIG. 14 illustrates a perspective view of the valve system, wherein valve member 226 is aligned in interlocking relationship with valve members 246, 266. Valve member 266 is shown in phantom in FIG. 14 to better illustrate the interlocking nature of the valve members.

As best shown in FIGS. 12 and 13, valve member 226 is similar in many respects to valve member 26. Valve member 226 includes upper face 227, which upper face includes first elevation 227A and a second elevation 227B, respectively. Valve member lower face 228 includes a first elevation 228A and a second elevation 228B, respectively. The respective elevations are interconnected at transition 229. Valve member 226 also includes a rounded outer edge portion 232, and a shaped inner edge portion 234. Inner edge portion 234 is shaped to be complementary with correspondingly-shaped inner edge portions of valve members 246, 266, respectively. Preferably, inner, edge portion 234 includes the curved (concave and convex) portions as previously described. As a result, these valve members interlockingly engage in a manner generally similar to that of valve members 26, 46, 66.

While structurally similar to valve members 26, 46, 66 in many respects, the valve members shown in FIGS. 12-14 illustrate optional variations. For example, the contour of valve members 226, 246, 266 is more sweeping than in the previous embodiment. As a result, while inner edge portions 34 of valve members 26, 46, 66 are subject to compression forces to remain sealingly engaged, respective inner edge portions 234 of valve members 226, 246, 266 are subject to tensile forces to remain sealingly engaged. In addition, the respective upper faces and lower faces of valve members 226, 246, 266 include feather extensions. Upper faces 227, 247, 267 are shown in FIG. 14, along with feather extensions 227C (FIG. 12), 247C, 267C, respectively. Corresponding feather extensions (e.g., extension 228C) are also present on the lower faces. It is believed that while the interlocking arrangement of the feather extensions of this embodiment will seal with the convex portion 236 as in the previously-described embodiment, they will also yield upon insertion of a medical device therethrough, and conform to seal around the device and with the adjacent valve members.

The valve members used herein are preferably formed from conventional elastomeric materials known for such use in the medical arts, such as silicone or polyurethane. Those skilled in the art will appreciate that other suitable compositions known for such purposes may be substituted, such as polyethylene and neoprene. The valve members can be formed to have any desired diameter and thickness, depending primarily upon the size of the housing, the size of an interventional device to be passed therethrough, and the desired pressure rating of the valve system. One skilled in the art can readily optimize the dimensions of the valve members in a valve system as described herein based upon the above-listed factors.

Valve members suitable for use in the present invention may be readily prepared utilizing techniques well known in the art, such as molding and casting. As stated, the valve members are all preferably identical to each other. Therefore, fabrication of such valve members is expected to be readily automated by conventional means. In addition, storage is facilitated since respective valve members need not be segregated according to shape. Notches, if present, may be molded or fabricated as described, or alternatively, may be simply punched, cut, or otherwise formed in the valve members by conventional means.

Although the figures and discussion above describe a valve formed from three valve members oriented rotationally 120 degrees from each other in the housing, the inventive valve system need not always include three valve members. Thus, more, or fewer, valve members may be utilized in a particular case. Preferably, in each such case, the valve members will be identical. Of course, routine modification will be made in each valve member in such instances to achieve the interlocking relationship described and shown herein. Thus, for example, if four identical valve members are utilized to form a seal, the valve members will be rotationally oriented 90 degrees from each other in the housing, rather than 120 degrees when three valve members are used. Similar modifications may be made to accommodate other numbers of valve members.

As still another alternative, the hemostasis valve system of the present invention can also include one or more valve disks. Such disk(s), if present, will typically be at either the proximal or distal end of the interlocking valve members arranged in the chamber. In one such embodiment, a disk can be provided in the housing body directly proximal of the interlocking valve members of the described valve. One such disk 190 is illustrated in FIG. 12. As shown, this disk includes a hole 192 through the radial center of the disk. This disk may be useful as an initial alignment tool to assist the wire guide or other structure to enter the valve substantially in a linear manner. In this instance, this disk would be arranged in the valve system in a manner such that it is the first valve structure encountered by the wire or device as it enters the proximal end of the introducer apparatus. If desired, the guide disk 190 may be frangible. Although the disk shown in FIG. 12 does not include a notch along the circumference of the disk, this feature can also be included if desired.

As yet another alternative, those skilled in the art will appreciate that although the disk-like annular configuration of the interlocked valve members as shown, e.g., in FIGS. 3, 8, 9, and 14 is preferred, this is not the only arrangement of valve members that is possible within the scope of the invention. For example, the respective valve members may be structured such that they can interlock to form a triangular, squared, or other outer perimetrical shape of a regular polygon. As further illustrated in said FIGS. 3, 8, 9, and 14, it is preferred that, upon engagement, the valve members align with each other to form generally flat upper and lower surfaces for the valve.

Those skilled in the art will appreciate that lubricants and other conventional additives for use with conventional check valves may also be utilized with the valve structure of the present invention. In particular, the use of conventional lubricants between the valve members may be desired to inhibit tackiness, friction, adhesion, etc., of adjacent valve members in well-known fashion, and to assist in the smooth movement of the interventional device through the holes.

It is therefore intended that the foregoing detailed description be regarded as illustrative rather than limiting, and that it be understood that it is the following claims, including all equivalents, that are intended to define the spirit and scope of this invention.

The invention claimed is:

1. A hemostasis valve system for controlling a flow of fluid therethrough, the valve system comprising:
a housing, said housing having a proximal end, a distal end, and a chamber disposed therebetween;
a valve disposed in said chamber, said valve comprising a plurality of elastomeric valve members, each of said valve members having opposing shaped first and second faces, a shaped inner edge portion, and a shaped outer edge portion, each of said faces comprising respective first and second elevations, said respective first and second elevations of each said face being generally parallel, wherein each of said shaped inner edge portions includes a concave curved portion and a convex curved portion, said respective first and second elevations of each valve member complementary upon engagement with a respective first and second elevation of another valve member upon engagement, and respective curved portions of each valve member complementary with curved portions of another valve member upon engagement, said valve members collectively structured and arranged such that said shaped faces and said shaped inner edges are engaged in an interlocking relationship, said valve members having sufficient elasticity to define an opening along said engaged inner edge portions upon passage therethrough of a medical interventional device.

2. The hemostasis valve system of claim 1, wherein said curved portions comprise a radius at each edge thereof at a juncture with a respective face.

3. The hemostasis valve system of claim 1, wherein each of said valve members includes a feather edge portion at at least one of said first and second faces.

4. The hemostasis valve system of claim 3, wherein each of said valve members includes a feather edge portion at each of said first and second faces.

5. The hemostasis valve system of claim 1, wherein said respective outer edge portions are rounded, and said valve members are interlocked such that a generally annular outer circumference is defined thereby.

6. The hemostasis valve system of claim 1, further comprising complementary structure disposed along each of said housing and said plurality of valve members for maintaining an arrangement of said valve members in said housing.

7. The hemostasis valve system of claim 6, wherein said complementary structure comprises a notch disposed at said outer edge portion of each of said valve members, and a plurality of ribs disposed along an inner surface of said housing, said ribs sized and shaped for receiving a respective notch.

8. The hemostasis valve system of claim 7, wherein said housing comprises a main body and an end cap, and wherein said ribs are disposed along an inner surface of said end cap.

9. The hemostasis valve system of claim 1, wherein each of said elastomeric valve members comprises an identical size and shape.

10. The hemostasis valve system of claim 9, wherein said valve comprises three identically-shaped valve members oriented rotationally 120 degrees from one another along an outer circumference of said valve.

11. The hemostasis valve system of claim 1, wherein said housing comprises a main body and an end cap, said chamber being disposed within an interior space of said end cap.

12. An apparatus for use in controlling a flow of fluid while introducing a medical interventional device into a body vessel of a patient, the apparatus comprising:
 a housing, said housing having a proximal end, a distal end, and a chamber disposed between said proximal end and distal end;
 a valve disposed in said housing chamber, said valve comprising a plurality of elastomeric valve members arranged in said chamber, each of said valve members having opposing shaped first and second faces, each of said first and second faces having a feather edge at each end thereof, a shaped inner edge portion, and a rounded outer edge portion, said valve members collectively structured and arranged such that said shaped faces and said shaped inner edges are engaged in interlocking relationship to define a generally annular structure, said shaped inner edge portions of said elastomeric members defining a sealable passageway; and
 a sheath, said sheath sized for passage through said sealable passageway, and extendable distally from said housing into said body vessel.

13. The apparatus of claim 12, wherein each of said shaped first and second faces comprises respective first and second generally parallel elevations, said respective first and second elevations of each valve member complementary with a respective first and second elevation of another valve member such that a generally flat outer surface for said annular structure is formed thereby, each of said shaped inner edge portions including a curved portion, said curved portion of each valve member complementary with a curved portion of another valve member.

14. The apparatus of claim 13, wherein said housing comprises a main body and an end cap, further comprising a plurality of ribs disposed along an inner surface of said end cap, each said valve member further including a notch at said rounded outer edge portion, said valve members being arranged in said housing such that said notches are receivable in respective ribs for maintaining a position of said valve members in said housing.

15. The apparatus of claim 13, wherein said plurality of valve members comprises three identically-shaped valve members oriented rotationally 120 degrees from one another along an outer circumference of said valve.

\* \* \* \* \*